United States Patent [19]

Hornung et al.

[11] Patent Number: 5,122,655
[45] Date of Patent: Jun. 16, 1992

[54] PARTICLE COUNTER FOR OPAQUE PARTICLES IN A FLUID STREAM

[75] Inventors: Dieter Hornung, Waldmohr; Paul Sahner, Dillingen/Saar; Jurgen Korb, Ottweiler-Furth; Michael Huppert, Heusweiler; Norbert Funk, Ingbert, all of Fed. Rep. of Germany

[73] Assignee: Hydac Technology GmbH, Sulzbach/Saar, Fed. Rep. of Germany

[21] Appl. No.: 587,351

[22] Filed: Sep. 24, 1990

[30] Foreign Application Priority Data

Oct. 24, 1989 [DE] Fed. Rep. of Germany ....... 8912584

[51] Int. Cl.⁵ .............................................. H01J 5/16
[52] U.S. Cl. ................................ 250/227.11; 250/573
[58] Field of Search ................... 250/227.21, 227.11, 250/573, 574, 576; 356/441, 442

[56] References Cited

U.S. PATENT DOCUMENTS

| | | | |
|---|---|---|---|
| 3,999,861 | 12/1976 | Bellinger | 250/576 |
| 4,201,471 | 5/1980 | Pitt et al. | 250/574 |
| 4,752,131 | 6/1988 | Eisenlauer et al. | 356/442 |

Primary Examiner—David C. Nelms
Assistant Examiner—Khaled Shami
Attorney, Agent, or Firm—Roylance, Abrams, Berdo & Goodman

[57] ABSTRACT

A particle counter operates by the opacity method and has a light barrier or electric eye. The light beam of the light barrier or electric eye penetrates a measuring channel for a fluid transverse to the passage of the fluid through the channel. An electronic analysis assembly is connected in series following the receiver of the light barrier or electric eye. The light emitting surface of the light barrier or electric eye is formed by the end surface of a light-emitting fiber. The light inlet or receiving surface is formed by the end surface of a receiving fiber. The end surface of light-emitting fiber lies in a first boundary surface of the measuring channel. The end surface of the receiving fiber is concentric to the light-emitting fiber end surface and is located in a second boundary surface of the measuring channel parallel to the first boundary surface.

20 Claims, 2 Drawing Sheets

PARTICLE COUNTER FOR OPAQUE PARTICLES IN A FLUID STREAM

FIELD OF THE INVENTION

The present invention relates to a particle counter operating according to the opacity method, especially for counting opaque particles in a fluid stream of a hydraulic or lubricating system. A light barrier or electric eye has a light beam penetrating through a measuring channel for the fluid, the light beam extending transverse to the longitudinal passage of the fluid through the channel. The particle counter has an electronic analysis device.

BACKGROUND OF THE INVENTION

Known particle counters operating according to the opacity method are very precise and costly laboratory devices. They include a high quality precision optic, which contributes to the high level of precision and makes these devices very sensitive to outside negative influences, especially vibrations or jarring, air humidity and temperature changes. The high cost results from costly operation and a costly electronic analysis device. Accordingly, these known particle counters are not even considered for use in industry, for instance in a hydraulic system.

SUMMARY OF THE INVENTION

An object of the present invention is to provide a particle counter employing the opacity method which is especially suitable for use in heavy industry.

Another object of the present invention is to provide an opacity method, particle counter which is relatively inexpensive to manufacture and operation, is rugged and insensitive to outside negative influences.

The foregoing objects are basically attained by a particle counter operating by an opacity method, particularly for metering and analyzing opaque particles in a fluid stream of a hydraulic or lubricating system, comprising a sensor body and a measuring channel in the sensor body for conveying a fluid stream to be analyzed along a longitudinal direction of the measuring channel. The measuring channel has first and second boundary surfaces which are parallel. A light-emitting fiber is immovably embedded and protected from moisture in the sensor body and has a first end surface lying in the first boundary surface. The first end surface emits a light beam into the measuring channel substantially traverse to the longitudinal direction. A light receiving fiber is immovably embedded and protected from moisture in the sensor body and has a second end surface lying in the second boundary surface. The second end surface is coaxially aligned with and opposite the first end surface for receiving the light beam emitted by the first end surface and across the measuring channel. A light sensitive receiver is optically coupled to the receiving fiber and contained in the sensor body. An electronic analysis assembly is connected in series to the receiver and is arranged in a housing structurally connected to the sensor body.

The particle counter of the present invention is protected from disturbances arising from vibration or jarring by embedding the simple electronic assembly in the sensor body. Such analyzer is capable of operating within a great range of temperatures. By arranging the electronic analysis assembly in a protective housing, which housing is preferably a housing of the IP 65 type, the required lack of susceptibility to interference of the electronic assembly can be attained at low cost. Since the particle counter according to the present invention combines all of the components required for its function into one single structural unit, it is very convenient for the customer or user; in other words, no skilled technical persons are required for its installation and initial setting in operation. Furthermore, the measuring system or "counter" according to the invention offers a complete and compact apparatus construction. Finally, by virtue of its simple construction, the analyzer according to the present invention fulfills both its optical and its electronic requirements at low cost.

By using the opacity method, the analyzer permits determination of the particulate sizes, dimensions, or magnitude, because the change of the light signal becomes greater the greater the area of the particle is. Thus, classes of particle sizes can be defined in a simple manner by electronic means. With a preferred embodiment, a few, for instance two to five, cumulative classes of particle sizes can be determined very precisely.

It is advantageous to construct the measuring channel in transverse, cross section with a trapezoidal shape with the length of the shorter of the two parallel sides equal to the diameter of the light-emitting fiber and with the angle between the two angularly oriented sides and the light-emitting fiber axis being equal the aperture angle of the light-emitting fiber. The construction for all practical purposes avoids reflections on the walls of the flow channel. Thus, the sensitivity of the sensor can be considerably improved.

Furthermore, on the basis of the good sensitivity of the sensor, the light-emitting optical fiber has a diameter in the range of $200\mu$–$300\mu$. The receiving/sensing fiber can have a smaller diameter than the light-emitting fiber, and preferably has approximately half the diameter of the light emitting fiber, for the same purpose. A good depth of focus is attained by spacing of the first and second boundary surfaces being in the size range of the light-emitting fiber diameter.

In one preferred embodiment, a light-emitting diode radiating a particularly intense infrared light is provided as the light source. The light from this source is conducted by the light-emitting fiber to the measuring channel.

In one preferred embodiment, a signal preamplifier is connected in series after the receiver of the light barrier or electric eye. The receiver of the optical signal is preferably a photodiode. A signal preprocessing stage can be connected in series after the signal preamplifier.

In order to be able to conveniently display the particle number and the state of operation of the system, the measurement device is constructed in a preferred embodiment shown in FIG. 1. In this case, the measurement results are displayed in the display. The diagnostic window contains display elements, especially light emitting diodes, which indicate whether the system is working in good order or whether a verification of one or more functions is required.

To simplify the handling and especially the assembly at the site of use, it is advantageous to arrange the sensor and the housing on one common base plate For use, then, only the fluid connection and the electric connection need to be made. The electronic assembly is not fed from a battery but rather from a socket power source.

A flow volume regulator can be provided in addition to the sensor, for precise determination of the volume flowing through the measuring channel. In such cases, it is advantageous to provide an additional auxiliary filter for the flow volume regulator.

Insofar as the system must be connected to a pressure line, it is advantageous to provide a pressure-reducing assembly. Such assembly is advantageously constructed with a pressure relief valve and a throttle valve.

Other objects, advantages and salient features of the present invention will become apparent from the following detailed description, which, taken in conjunction with the annexed drawings, discloses a preferred embodiment of the present invention.

BRIEF DESCRIPTION OF THE DRAWINGS

Referring to the drawings form a part of this disclosure.

DETAILED DESCRIPTION OF THE INVENTION

Figure 2:
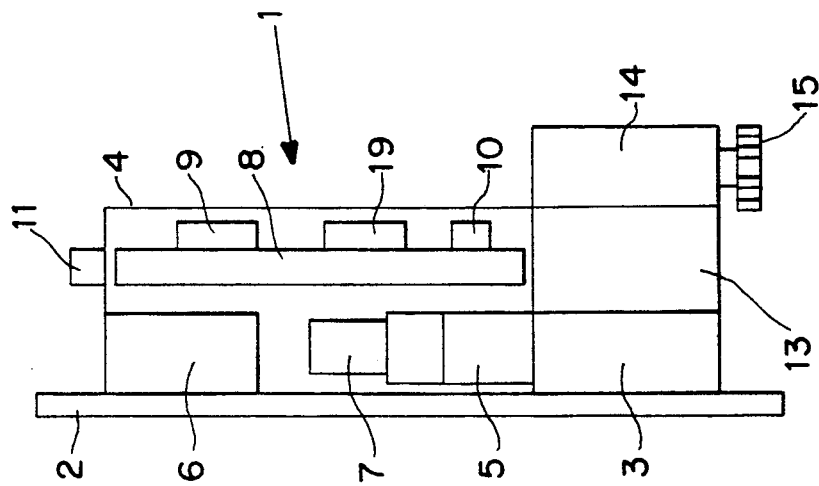
FIG. 2 is a side elevational view of the particle counter of FIG. 1.

A low cost, particle counter or meter according to the present invention, indicated in its entirety as 1, is useful in heavy industry, especially in hydraulic or lubricating systems. The analyzer, as shown in the exemplary embodiment, has a rectangular plate 2. A sensor 3 in the form of a parallelipiped is arranged on base plate 2 and is connected to a housing 4 of the IP 65 protective housing type. Housing 4 is connected detachably with the base plate, and houses a signal preamplifier unit 5, a socket power source 6 for supplying the power to the electronic assembly and the sensor 3, a signal preprocessing stage 7, and an analysis and display module 8.

At its top, arranged parallel to base plate 2, housing 4 has three rectangular apertures. Two of the rectangular apertures serve as display windows 9. One of the rectangular apertures serves as a diagnostic window 10. In both display windows 9 the results of the measurement are displayed. The diagnostic window 10 permits viewing of light-emitting diodes to facilitate monitoring of the operation of the whole system. These light-emitting diodes indicate, for instance, whether the system or device is ready for operation or is not ready for operation, whether the diode current of the light-emitting diode of sensor 3 is too small or too large, whether an overbias or overload is present, and whether some maintenance, especially cleaning of sensor 3, is required in the near future.

In the exemplary embodiment, housing 4 is also provided with an interface 11. The interface permits conveying the measured data to a data acquisition assembly and to communicate with a robotic control unit or the like.

The device is completely capable of functioning with the structural unit described above. In the exemplary embodiment, however, the output from a measuring channel 12 (FIG. 3) of sensor 3 is connected with an auxiliary filter 13. A flow volume regulator 14 is connected in series after or downstream of filter 13. Auxiliary filter 13 and flow volume regulator 14 have block shapes, in the exemplary embodiment, identical to the shape of sensor 3, and are arranged stacked over sensor 3 as shown in FIG. 2. A manual control knob 15 serves to set the flow volume regulator 14 so that the volume flowing through measuring channel 12 can be controlled precisely.

Figure 1:
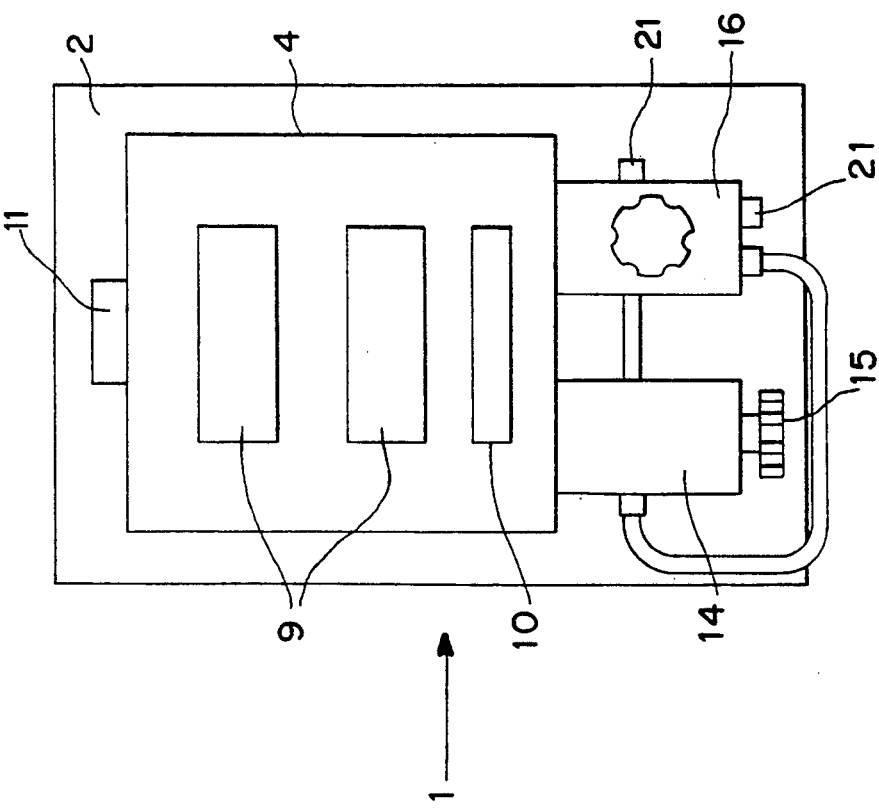
FIG. 1 is a plan view of a particle counter according to an exemplary embodiment of the present invention.

Furthermore, in the exemplary embodiment, a pressure-reducing unit 16 is arranged on the base plate 2, adjacent to the stack formed of sensor 3, auxiliary filter 13 and flow volume regulator 14, so that the system can be connected to a pressure line. The pressure-reducing unit includes a throttle valve and a pressure relief valve. As shown in FIG. 1, the input of sensor 3 and the output of flow volume regulator 14 are each connected through a conduit with pressure-reducing unit 16, which has two connections 21. The particle counter 1 is connected with the hydraulic or lubricating system through connectors 21.

Figure 3:
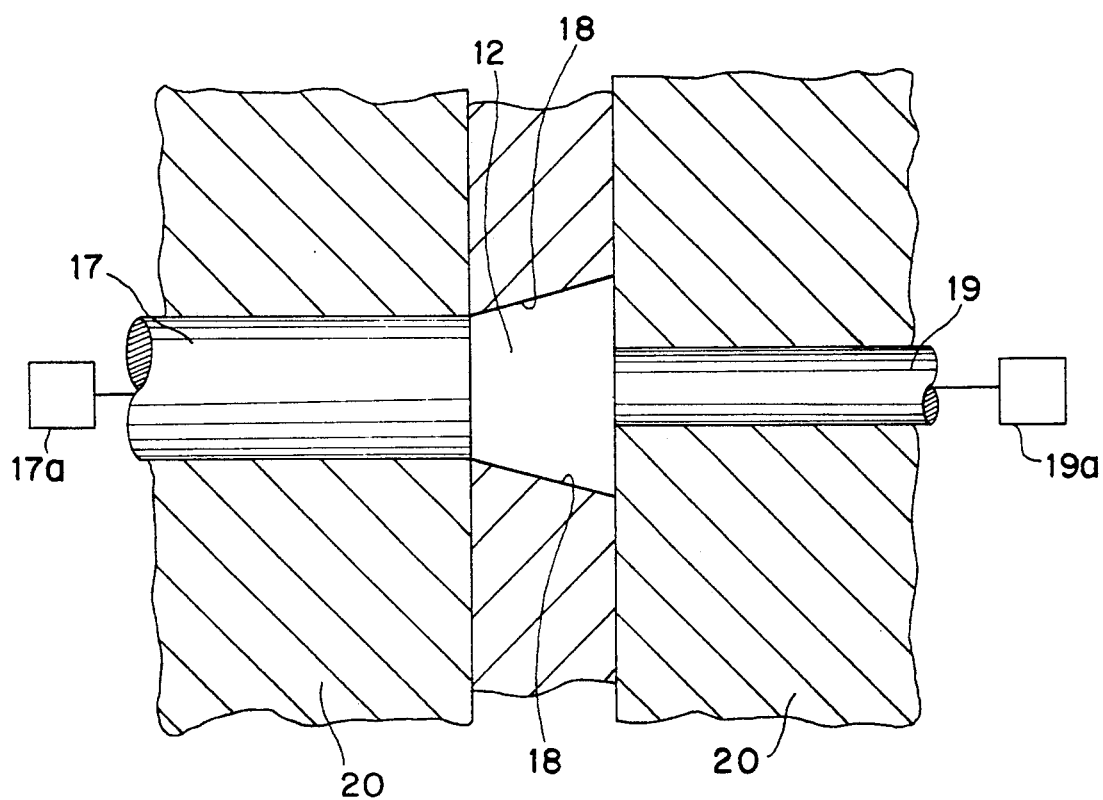
FIG. 3 is a partial, enlarged, side elevational view in section of the particle counter of FIG. 1 through the measuring channel and optics of the light barrier or electric eye.

Measuring channel 12 in sensor 3 becomes narrower or tapers as it approaches the measuring point and, at least at that point, is of trapezoidal shape, as shown in FIG. 3. The shorter of the two sides parallel to one another is formed by the end surface of a light-emitting fiber 17 formed by a glass fiber. In the exemplary embodiment, fiber 17 has an outside diameter of 300$\mu$, but can be in the range of 200$\mu$ to 300$\mu$. The other end of light-emitting fiber 17 receives an extraordinarily intense infrared light from a light-emitting diode serving as light source.

The flat surfaces 18 of flow passage 12 form the two angularly oriented sides of the trapezoid. The straight end segment of light-emitting fiber 17 is bounded by measuring channel 12. Flat surfaces 18 and the longitudinal axis of the straight end segment of light-emitting fiber 17 define an angle $\theta_A$, which is predetermined to be identical to the aperture angle of the light-emitting fiber 17. Reflection of the light emanating from the end of light-emitting fiber on the flat surfaces 18 is thus prevented. The avoidance of such reflections considerably increases the sensitivity (detective capacity) of particle counter 1. The distance between the two parallel sides of the trapezoid is preferably in the size range of light-emitting fiber 17.

The boundary surface of channel 12 extending parallel to the end surface of light-emitting fiber 17 is formed partially by the end surface of a light receiving fiber 19. The straight end segment of receiving fiber 19 engages the channel 12 to perform the measurement, and is arranged in a straight line or coaxial relative to light-emitting fiber 17. The diameter of receiving fiber 19, formed by a special glass fiber, is approximately half the diameter of light-emitting fiber 17. The other end of receiving fiber 19 is coupled with a photodiode, which photodiode forms the receiver of the miniature light barrier or electric eye. The light beam penetrates measuring channel 12 transverse to its length.

Light-emitting fiber 17 and receiving fiber 19 are completely embedded in sensor body 20 with the help of epoxy resin. This sensor body 20 also includes measuring channel 12, as well as the light-emitting diode 17a serving as a light source and the photodiode 19a serving as a receiver. Sensor 13 is thereby protected from moisture and other negative influences, and is insensitive to vibration or jarring and the like. Sensor body 20 is located in a protective housing.

The particle counter operates in the following manner. Measuring channel 12 conveys the fluid stream containing the particulate matter to be counted flowing through it. The thin narrow light beam of the light barrier or electric eye emanating from light-emitting fiber 17 and penetrating measuring channel 12 is directed to the receiving fiber 19. By virtue of the very small diameter of measuring channel 12 and because channel 12 is thus very small in comparison with the light barrier or electric eye, one can assume that most of the particulate matter carried along in the fluid is detected by the light beam and that the receiving surface of receiving fiber 19, dependent upon the extent of particulate matter, is more or less strongly shaded. The light comes into receiving fiber 19 and reaches the photodiode, by which the deviations of brightness are converted into correspondingly deviating electric signals.

Between two adjacent particles, the light impacting the receiving surface of receiving fiber 19 is attenuated only by the turbidity of the fluid. The signal preamplifier unit 5 permits scanning of the fluids of various different levels of turbidity, since it sets the output signal of the photodiode automatically at a value which generates a predetermined signal depth. The reinforced amplified signal then proceeds to the signal preprocessing stage 7, which forms the signals produced by the degrees of shading and then feeds a pulse light analyzer found in the analysis and display module. With the help of this pulse light analyzer, the particle size could be arranged in very precise classes, since the measure of the shading depends upon the area of the particle. After the signal valuation by the pulse level analyzer, the signals move to the subsequent series-connected meters of analysis and display module 8. This module is set on a precise gate time or count time, and indicates the number of particles ascertained in this time period in display windows 9 for display.

Through the interface 11, the particle counter can be addressed by a robotic unit, for instance memory programmable unit, machine control unit or a controlling or monitoring computer. Also, data could subsequently be fed through interface 11 to an overriding control level. Furthermore, setting of parameters and monitoring of the particle counter is also possible.

While particle counter 1 is in operation, monitoring signals locally indicate the instrument status and the individual functions, and those monitoring signals are visible in the diagnostic window 10. For instance the rate and dimensions of the current of the diode producing the light of the light barrier or electric eye, the measure of the signal preamplification indicated by the signal preamplification unit 5, and whether cleaning of the measuring channel will soon be required are displayed.

While a particular embodiment has been chosen to illustrate the invention, it will be understood by those skilled in the art that various changes and modifications can be made therein without departing from the scope of the invention as defined in the appended claims.

What is claimed is:

1. A particle counter operating by an opacity method, particularly for measuring and analyzing opaque particles in a fluid stream of a hydraulic or lubricating system, comprising:
   a sensor body;
   a measuring channel in said sensor body for conveying a fluid stream to be analyzed along a longitudinal direction of said measuring channel, said measuring channel having first and second boundary surfaces, said boundary surfaces being parallel;
   a light-emitting fiber completely embedded in said sensor body by first means for protecting said light-emitting fiber from moisture and for connecting said light-emitting fiber immovably relative to said sensor body, said light-emitting fiber having a first end surface lying in said first boundary surface, said first end surface emitting a light beam into said measuring channel substantially transverse to said longitudinal direction;
   a light receiving fiber completely embedded in said sensor body by second means for protecting said light receiving fiber from moisture and for connecting said light receiving fiber immovably relative to said sensor body, said light receiving fiber having a second end surface lying in said second boundary surface, said second end surface being coaxially aligned with and opposite said first end surface for receiving the light beam emitted by said first end surface and across said measuring channel;
   a light sensitive receiver optically coupled to said receiving fiber and contained in said sensor body; and
   an electronic analysis assembly connected in series to said receiver and arranged in a housing, said housing being structurally connected to said sensor body.

2. A particle counter according to claim 1 wherein said measuring channel has a trapezoidal transverse cross-sectional shape adjacent said first and second end surfaces, said trapezoidal shape having shorter and longer parallel sides connected by two angularly oriented sides, said shorter side forming said first boundary surface and having a length equal to a diameter of said light-emitting fiber, each of said angularly oriented sides forming an angle with a longitudinal axis of said light-emitting fiber equal to an aperture angle of said light-emitting fiber.

3. A particle counter according to claim 2 wherein said diameter of said light-emitting fiber is between about 200µ and about 300µ.

4. A particle counter according to claim 3 wherein said first and second boundary surfaces are spaced by a distance between about 200µ and about 300µ.

5. A particle counter according to claim 1 wherein said first and second boundary surfaces are spaced by a distance substantially equal to a diameter of said light-emitting fiber.

6. A particle counter according to claim 1 wherein said light receiving fiber has a diameter smaller than a diameter of said light-emitting fiber.

7. A particle counter according to claim 6 wherein said diameter of said light receiving fiber is approximately one half said diameter of said light-emitting fiber.

8. A particle counter according to claim 1 wherein said light-emitting fiber is coupled to a light source comprising a light-emitting diode emitting infrared light coupled to said measuring channel through said light-emitting fiber.

9. A particle counter according to claim 8 wherein said light-emitting diode is integrated into said sensor body.

10. A particle counter according to claim 1 wherein said receiver is connected downstream in series to a signal preamplifier; and
    said signal preamplifier is connected downstream in series to a signal preprocessing stage.

11. A particle counter according to claim 1 wherein said electronic analysis assembly comprises an analysis and display module.

12. A particle counter according to claim 11 said housing comprises apertures sealed by at least one diagnostic window and at least one display window.

13. A particle counter according to claim 1 wherein said sensor body and said housing are mounted on a common base plate.

14. A particle counter according to claim 1 wherein said measuring channel comprises an output connected to a flow volume regulator.

15. A particle counter according to claim 14 wherein a filter is connected to said sensor body and said flow volume regulator.

16. A particle counter according to claim 1 wherein said sensor body is attached to a pressure reducing unit, said pressure reducing unit being connected to said housing.

17. A particle counter according to claim 16 wherein said pressure reducing unit comprises a throttle valve and a pressure relief valve.

18. A particle counter operating by an opacity method, particularly for measuring and analyzing opaque particles in a fluid stream of a hydraulic or lubricating system, comprising:
 a sensor body;
 a measuring channel in said sensor body for conveying a fluid stream to be analyzed along a longitudinal direction of said measuring channel, said measuring channel having first and second boundary surfaces, said boundary surfaces being parallel;
 a light-emitting fiber immovably embedded and protected from moisture in said sensor body and having a first end surface lying in said first boundary surface, said first end surface emitting a light beam into said measuring channel substantially transverse to said longitudinal direction;
 a light receiving fiber immovably embedded and protected from moisture in said sensor body and having a second end surface lying in said second boundary surface, said second end surface being coaxially aligned with and opposite said first end surface for receiving the light beam emitted by said first end surface and across said measuring channel;
 a measuring channel section having a trapezoidal transverse cross-sectional shape adjacent said first and second end surfaces, said trapezoidal shape having shorter and longer parallel sides connected by two angularly oriented sides, said shorter side forming said first boundary surface and having a length equal to a diameter of said light-emitting fiber, each of said angularly oriented sides forming an angle with a longitudinal axis of said light-emitting fiber equal to an aperture angle of said light-emitting fiber;
 a light sensitive receiver optically coupled to said receiving fiber and contained in said sensor body; and
 an electronic analysis assembly connected in series to said receiver and arranged in a housing, said housing being structurally connected to said sensor body.

19. A particle counter according to claim 18 wherein said diameter of said light-emitting fiber is between about 200μ and about 300μ.

20. A particle counter according to claim 19 wherein said first and second boundary surfaces are spaced by a distance between about 200μ and about 300μ.

* * * * *